United States Patent
Redoules et al.

(10) Patent No.: US 9,493,401 B2
(45) Date of Patent: Nov. 15, 2016

(54) GLUTAMATE DERIVATIVES FOR TOPICAL USE AS IMMUNOMODULATORY ACTIVE INGREDIENT

(71) Applicant: PIERRE FABRE DERMO-COSMETIQUE, Boulogne-Billancourt (FR)

(72) Inventors: Daniel Redoules, Toulouse (FR); Sylvie Daunes-Marion, Toulouse (FR); Stéphane Poigny, Saubens (FR); Marie-Françoise Aries, Escalquens (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 14/653,682

(22) PCT Filed: Dec. 19, 2013

(86) PCT No.: PCT/EP2013/077320
§ 371 (c)(1),
(2) Date: Jun. 18, 2015

(87) PCT Pub. No.: WO2014/096155
PCT Pub. Date: Jun. 26, 2014

(65) Prior Publication Data
US 2016/0060208 A1 Mar. 3, 2016

(30) Foreign Application Priority Data
Dec. 19, 2012 (FR) .................................... 12 62329

(51) Int. Cl.
*C07C 229/08* (2006.01)
*A61K 9/00* (2006.01)
*C07C 227/18* (2006.01)
*A61K 31/221* (2006.01)
*C07C 229/24* (2006.01)

(52) U.S. Cl.
CPC ........... *C07C 229/08* (2013.01); *A61K 9/0014* (2013.01); *A61K 31/221* (2013.01); *C07C 227/18* (2013.01); *C07C 229/24* (2013.01)

(58) Field of Classification Search
None
See application file for complete search history.

(56) References Cited

U.S. PATENT DOCUMENTS 3,285,953 A 11/1966 Wasserman et al.
3,669,717 A 6/1972 Akamatsu et al.

FOREIGN PATENT DOCUMENTS

EP 0572167 A1 12/1993
FR 1427996 A 2/1966

OTHER PUBLICATIONS

Database Caplus in STN, Acc. No. 1963:475626, Huang et al., Yaoxue Xuebao (1963), 10(6), pp. 359-364 (abstract).*
Database Caplus in STN, Acc. No. 1971:553027, Akamatsu et al., DE 2047048 A (Apr. 15, 1971) (abstract).*
Allam et al., "Recent Highlights in the Pathophysiology of Atopic Eczema," International Archives of Allergy and Immunology, vol. 136, 2005 (published online Feb. 8, 2005), pp. 191-197.
De Prost et al., "Double-blind Randomized Placebo-Controlled Trial of Local Cyclosporine in Atopic Dermatitis," Arch Dermatol, vol. 125, Apr. 1989, p. 570.
Ho et al., "Saftey and Efficacy of Nonsteroid Pimecrolimus Cream 1% in the Treatment of Atopic Dermatitis in Infants," The Journal of Pediatrics, vol. 142, No. 2, Feb. 1, 2003, XP009006977, pp. 155-162.
Howell et al., "Cytokine modulation of atopic dermatitis filaggrin skin expression," J. Allergy Clin Immunol, vol. 120, No. 1, Jul. 2007, pp. 150-155.
Imokawa et al., "Decreased Level of Ceramides in Stratum Corneum of Atopic Dermatitis: An Etiologic Factor in Atopic Dry Skin?," The Journal of Investigative Dermatology, vol. 96, No. 4, Apr. 1991, pp. 523-526.
International Search Report dated Mar. 18, 2014, for International Application No. PCT/EP2013/077320.
Klieger et al., "A simplified process and reactions of α-hemi esterification of carbobenzoxy-L-glutaminic acid," Liebig's Annalen vol. 655, Jan. 1, 1962, pp. 195-210.
Koga et al., "Possible Pathogenic Role of TH17 Cells for Atopic Dermatitis," Journal of Investigative Dermatology, vol. 128, 2008 (Published online Apr. 24, 2008), pp. 2625-2630.
Novak et al., "Dichotomic Nature of Atopic Dermatitis . . . : The Dichotomy of Extrinsic and Intrinsic Atopic Dermatitis" The Journal of Investigative Dermatology, vol. 119, No. 4, Oct. 2002, p. 870-875.
Poché et al., "An Unconventional Method for Purifying the N-Carboxyanhydride Derivatives of γ-ALKYL-L-Glutamates," Synthetic Communications, vol. 29, No. 5, 1999 (published online Sep. 17, 2007), pp. 843-854.
Reitamo et al., "Topical Noncorticosteroid Immunomodulation in the Treatment of Atopic Dermatitis," Am J Clin Dermatol, vol. 3, No. 6, 2002, pp. 381-388.
Von Bubnoff et al., "Natural Killer cells in atopic and autoimmune diseases of the skin," J Allergy Clin Immunol, vol. 125, No. 1, Jan. 2010, pp. 60-68.

* cited by examiner

*Primary Examiner* — Brian J Davis
(74) *Attorney, Agent, or Firm* — Birch, Stewart, Kolasch & Birch, LLP

(57) ABSTRACT

The present invention relates to L-glutamate-derived compounds of general formula (I) in which the R radical is a linear or branched $C_5$ to $C_2$ alkyl group, .—or the benzyl radical, .—or the phenethyl radical, for topical use as a medicament (or as a dermatological active ingredient) intended for the treatment and/or prevention of inflammatory dermatoses.

8 Claims, 3 Drawing Sheets

| CD4+ lymphocytes: cytokines induced per 300 ng/ml SEB (24h) | | % of activity of Example 12 on the production of cytokines | | | |
|---|---|---|---|---|---|
| | | Evaluated concentrations | | | |
| | | 10μM | 30μM | 100μM | 300μM |
| Th1 response | IL2 | -16 | -29 | -34 | -43 |
| | IL6 | -12 | -34 | -37 | -44 |
| | IL12 | 22 | -3 | 24 | 52 |
| | IFNα | -16 | -34 | -57 | -77 |
| | IL1α | -43 | -55 | -66 | -80 |
| | TNFα | -23 | -31 | -17 | -18 |
| Th2 response | IL4 | -22 | -40 | -54 | -69 |
| | IL5 | -44 | -68 | -68 | -77 |
| | IL10 | -16 | -33 | -62 | -87 |
| | IL13 | -62 | -75 | -78 | -84 |
| Th17 response | IL17 | -72 | -74 | -79 | -86 |

GLUTAMATE DERIVATIVES FOR TOPICAL USE AS IMMUNOMODULATORY ACTIVE INGREDIENT

The field of the present invention relates to novel glutamate derivatives and to their use as an immunomodulatory active ingredient.

More particularly, the present invention relates to novel interesting compositions for their topical use in treating and preventing inflammatory dermatoses such as atopic dermatitis, contact eczema, acne, seborrheic dermatitis, rosacea or psoriasis.

The applications described to this day relating to esters of glutamic acid target inter alia cosmetic compositions intended to promote capillary growth (EP0572167). Other anteriorities describe certain esters of glutamic acid as synthesis intermediates.

Atopic dermatitis (AD) is an inflammatory chronic pathology which affects close to 20% of children and the prevalence of which is sharply increasing in developed countries. It is a plurifactorial disease, the phenotype of which is modulated by factors both coming under genetic and immunological factors but also hormonal and environmental, which are combined in diverse ways and expressed in a very polymorphous way in patients. Presently, the form of IgE-dependent allergic AD is distinguished, which affects about 80% of the patients and the nonallergic form which concerns a minority of patients in which a normal IgE serum concentration is again found. Further, epidemiological studies seem to indicate that AD begins in children in a nonallergic form and then develops towards the allergic form (Novak N et al., Dichotomic nature of atopic dermatitis reflected by combined analysis of monocyte immunophenotyping and single nucleotide polymorphisms of the interleukin-4/interleukin-13 receptor gene: the dichotomy of extrinsic and intrinsic atopic dermatitis, J Invest Dermatol. 2002 October; 119(4):870-5, 2002; Allam J P et al., Recent highlights in the pathophysiology of atopic eczema, Int Arch Allergy Immunol. 2005 February; 136(2):191-7).

Immunologically, development of the inflammatory lesion occurs after a phase of sensitization with allergens present in the environment either protein allergens (case of atopic dermatitis) or chemical allergens (allergic contact eczema). The eczema lesions occur, after new exposure to the allergen and are due to infiltration of the inflammatory cells of the blood into the skin. Activated CD4$^+$ T lymphocyte sub-populations during this phase have a particular profile for producing cytokines of the Th2 type (IL-4, IL-5 and IL-13) and are involved in the recruitment of effector cells of the delayed reaction and cause reductions in the synthesis of filaggrin and ceramides which characterize the abnormalities of the cutaneous barrier observed in patients bearing AD (Cytokine modulation of atopic dermatitis filaggrin skin expression, Howell M D et al., J Allergy Clin Immunol. 2007 July; 120(1):150-5), (Imokawa et al., Decreased level of ceramides in stratum corneum of atopic dermatitis: an etiologic factor in atopicdry skin, J Invest Dermatol. 1991 April; 96(4):523-6 1991). In this context, alteration of the cutaneous barrier promotes penetration of the allergens and activation of the specific T lymphocytes. Further, these cytokines are responsible for the synthesis of IgE by plasmocytes originating from B lymphocytes activated by the antigen. Thus, there exists a vicious circle for sustaining the allergic response. The cells showing antigens loaded with IgE have a much larger amount of epitopes to the lymphocytes and promote an IgE response.

The production of IL-4 characterizes the TH2 differentiation, which plays a crucial role in the development of the IgE response.

Further, it was shown that the TH17 lymphocytes produce pro-inflammatory cytokines and play a significant role in the pathogenesis of AD. Indeed, in a pharmaco-clinical study, the authors find an increase in the percentage of TH17 lymphocytes in blood and in the skin of subjects bearing AD, and that this increase is positively and significantly correlated with the seriousness of AD (Koga C, Kabashima K, Kobayashi M, Tokura Y. Possible pathogenic role of TH17 cells for atopic dermatitis. J Investig Dermatol 2008; 128: 2625-30). Finally, mention may be made of the predominance of the TH1 response in chronic AD lesions (von Bubnoff et al, Natural killer cells in atopic and autoimmune diseases of the skin, J Allergy Clin Immunol. 2010 January; 125(1):60-8).

Conventional treatments of atopic dermatitis notably use dermocorticoids or immunosuppressors, molecules capable of suppressing the T lymphocyte immune response.

Clinical efficiencies of immunosuppressors like tacrolimus or pimecrolimus have been established by many studies:

De Prost et al., double-blind randomized placebo—controlled trial of local cyclosporine in atopic dermatitis, Arch Dermatol. 1989 April; 125(4):570;

Ho V C et al., Safety and efficacy of nonsteroid pimecrolimus cream 1% in the treatment of atopic dermatitis in infants, J Pediatr. 2003 February; 142(2):155-62;

Reitamo et al., Topical noncorticosteroid immunomodulation in the treatment of atopic dermatitis, Am J Clin Dermatol. 2002; 3(6):381-8. Review.

However, dermocorticoids or immunosuppressors are not without any undesirable effects notably in children.

AD is characterized by repeated rashes for several years. It develops by outbreaks interrupted with spontaneous remissions.

The disease should be treated in the long term. Thus there exists a need and a strong demand for demonstrating therapeutic alternatives to these inflammatory dermatoses. The use of immunomodulators via a local route, is today part of the therapeutic arsenal for treating atopic dermatitis as well as other dermatoses such as psoriasis or contact eczema.

Conducting active research on inflammatory dermatoses, the applicant noticed in a particularly surprising way that L-glutamate derivatives of general formula I had properties both of modulating the immune response and modulating the inflammatory response.

Within the scope of this invention, the development of molecules derived from L-glutamate (monoester in position 5 of L-glutamic acid), designed for topical applications and capable of modulating the activation of the lymphocyte and keratinocyte populations was therefore contemplated.

In the sense of the present invention, by "L-glutamate derivatives" are meant compounds which fit the following general formula I:

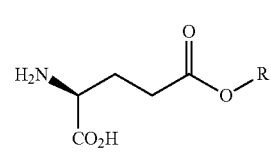

I wherein R represents:
  a linear or branched $C_5$-$C_{25}$ and preferably $C_5$-$C_{14}$ alkyl group;
  or the benzyl radical,
  or the phenethyl radical,
  or a radical selected from the group consisting of isoprenyl, geranyl, farnesyl and phytyl radicals,
for their topical use as a dermatological active ingredient intended for treating and/or preventing inflammatory diseases of the skin.

According to a particular embodiment of the invention, the compounds of general formula I are those for which the radical R represents a linear or branched $C_5$-$C_{25}$ and preferably $C_7$-$C_{14}$ alkyl group.

By "alkyl radical", is meant in the sense of the present invention a saturated linear or branched aliphatic hydrocarbon chain and comprising the specified number of carbon atoms.

By "benzyl radical", is meant in the sense of the present invention: —$CH_2$—$C_6H_5$.

By "phenethyl radical", is meant in the sense of the present invention; —$CH_2$—$CH_2$—$C_6H_5$.

According to another aspect of the invention, the dermatological uses and compositions intended for treating and/or preventing inflammatory dermatoses, also concerning glutamate derivatives not only as pure L enantiomers, but also in the form of all the mixtures of two D and L enantiomers with however preferably a predominant fraction of L enantiomer.

The compounds according to the invention have immunomodulatory efficiencies superior to those obtained with glutamic acid alone towards the lymphocyte responses TH1, TH2 and TH17 (FIGS. 1a, 1b and 1c respectively obtained with the compound of Example 3). These derivatives therefore have a potential benefit as an immunoregulator in patients affected with inflammatory skin diseases such as atopic dermatitis, contact eczema, or psoriasis.

In a particular embodiment of the invention, the activity of the derivatives of general formula I was evaluated according to their chain length. The activity is optimum from compounds for which the chain lengths are comprised between $C_5$ and $C_{14}$ (FIGS. 2a and 2b). According to another embodiment of the invention, the presence of a short branched chain gives the possibility of maintaining the immunomodulatory activity comparatively with the compound according to Example 3 (FIG. 2c).

In a preferred embodiment of the invention, the compounds of formula I are the novel compounds:
  5(3, 7-dimethyloctyl)-L-glutamate or 2-amino-5(3,7-dimethyloctyloxy)-5-oxopentanoic acid
  5(nonan-2-yl)-L-glutamate or 2-amino-5(nonan-2-yloxy)-5-oxopentanoic acid
  5(nonan-5-yl)-L-glutamate or 2-amino-5(nonan-5-yloxy)-5-oxopentanoic acid
  5(2-hexyldecyl)-L-glutamate or 2-amino-5(2-hexyldecyloxy)-5-oxopentanoic acid
  5(2-ethylhexyl)-L-glutamate or 2-amino-5(2-ethylhexyloxy)-5-oxopentanoic acid Moreover, the compounds of formula I according to the invention also show an anti-inflammatory activity which is not again found with glutamic acid (FIG. 4 for the compound according to Example 3). This additional activity of these derivatives widens their field of therapeutic applications to other inflammatory dermatoses such as acne, rosacea as well as seborrheic dermatitis.

The derivatives according to the invention therefore have a benefit as an anti-inflammatory and immunoregulating agent in patients affected with inflammatory dermatoses such as atopic dermatitis, contact eczema, acne, seborrheic dermatitis, rosacea or psoriasis.

According to a particular embodiment of the invention, the compounds of general formula (I) may be selected from the list of the following compounds:
  5-(n-pentyl)-L-glutamate or 2-amino-5-oxo-5-(pentyloxy)pentanoic acid
  5-(n-hexyl)-L-glutamate or 2-amino-5-(hexyloxy)-5-oxopentanoic acid
  5-(n-nonyl)-L-glutamate or 2-amino-5-(nonyloxy)-5-oxopentanoic acid
  5-(n-dodecyl)-L-glutamate or 2-amino-5-(dodecyloxy)-5-oxopentanoic acid
  5-(n-tetradecyl)-L-glutamate or 2-amino-5-oxo-5(tetradecyl)pentanoic acid
  5-(n-hexadecyl)-L-glutamate or 2-amino-5-(hexadecyloxy)-5-oxopentanoic acid
  5-(n-octadecyl)-L-glutamate or 2-amino-5-(octadecyloxy)-5-oxopentanoic acid
  5-(3,7-dimethyloctyl)-L-glutamate or 2-amino-5(3,7-dimethyloctyloxy)-5-oxo-pentanoic acid
  5-(nonan-2-yl)-L-glutamate or 2-amino-5(nonan-2-yloxy)-5-oxopentanoic acid
  5-(nonan-5-yl)-L-glutamate or 2-amino-5(nonan-5-yloxy)-5-oxopentanoic acid
  5-(2-hexyldecyl)-L-glutamate or 2-amino-5(2-hexyldecyloxy)-5-oxopentanoic acid
  5-(2-ethylhexyl)-L-glutamate or 2-amino-5(2-ethylhexyloxy)-5-oxopentanoic acid The present invention relates to the compounds of general formula (I) for their use as an active ingredient/immunomodulatory and/or antiinflammatory drug.

The present invention also relates to topical use of dermatological or cosmetic compositions comprising a compound of general formula (I) in treating and/or preventing inflammatory dermatoses.

According to another feature of the invention, the immunomodulatory active appears as a dermatological or cosmetic composition containing at least one compound of formula I in an amount from 0.01% to 20%, preferably from 0.1% to 10% by weight, and more particularly from 1% to 5% by weight based on the total weight of the composition.

The dermatological or cosmetic composition according to the invention further comprises one or several dermatologically or cosmetically compatible usual excipients.

The dermatologically or cosmetically compatible excipients may be any excipient among those known to one skilled in the art in order to obtain a composition for topical application as a milk, a cream, a balm, an oil, a lotion, a gel, a foaming gel, an ointment, a spray, etc.

The invention also relates to a method for preparing compounds of formula I, characterized in that N-alpha-benzylcarbonyl-L-glutamic acid alpha-benzyl ester is reacted with an alcohol of formula R—OH wherein R has the meaning given earlier and the obtained product is de-protected by catalytic hydrogenation.

The invention will be better understood upon reading the results below which illustrate it without limiting its scope.

A/PHARMACOLOGICAL EVALUATION

A.1-Demonstration of the immuno-regulatory activity: Study of the secretion of IL2, IL-4 and IL-17 for the lymphocyte responses TH1, TH2 and TH17 respectively.

The pharmacological activities of the esters according to the invention have been demonstrated as follows:

Blood mononuclear human cells (Peripheral Blood Mononuclear Cells, PBMC) are isolated from Buffy-Coat bags from the "Etablissement Français du Sang" (EFS) Pyrénées Méditerranée, on a Ficoll gradient (a medium for separating lymphocytes, density 1.077 g/ml); the $CD4^+$ lymphocytes are purified from this cell population by magnetic immunoselection ($CD4^+$ T Cell Isolation Kit II, Ref. 130-091-155 Miltenyi Biotec) and then distributed in 24-well plates in some 5% FCS RPMI culture medium; they are then pre-incubated with the active ingredients to be evaluated for 1 hour and then stimulated for 24 hours with 300 ng/ml of SEB (Staphylococcus aureus enterotoxin B). The dosages of lymphocyte cytokines are conducted from a sample taken from the supernatant according to the following methods:

IL2 (TH1), IL4 (TH2), are evaluated in flow cytometry by CBA (Ref. 550749, BECTON Dickinson),
IL17 (TH17) is evaluated by ELISA, Human IL17 Quantikine (Ref. D1700, R&D Systems),
IL2 (TH1) is also evaluated by ELISA, Duoset IL2 (Ref. DY202, R&D Systems).

Figure 1A:
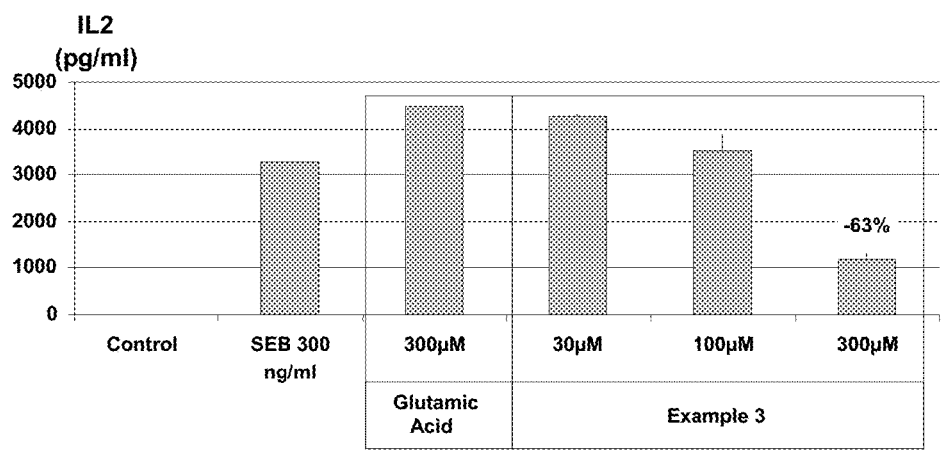
FIGS. 1a, 1b and 1c: Demonstration of the immunoregulatory activity of the compound according to Example 3 towards secretions of IL-2 (1a), IL-4 (1b) and IL-17 (1c) by human lymphocytes.
Figure 1B:
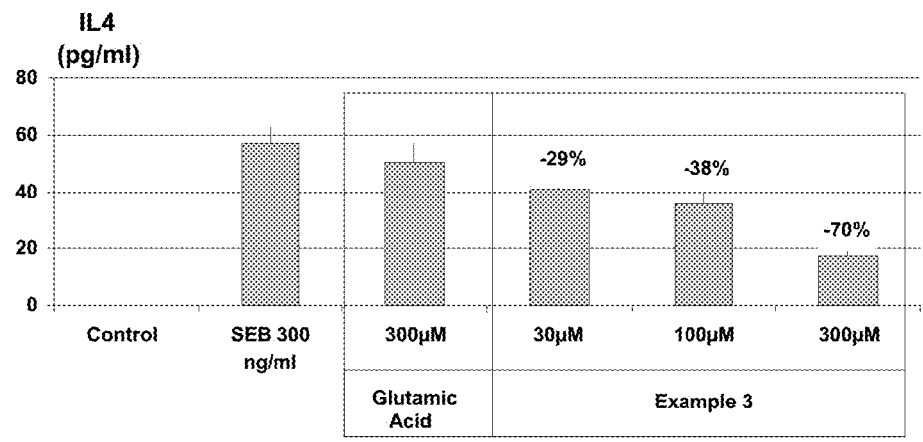
Figure 1C:
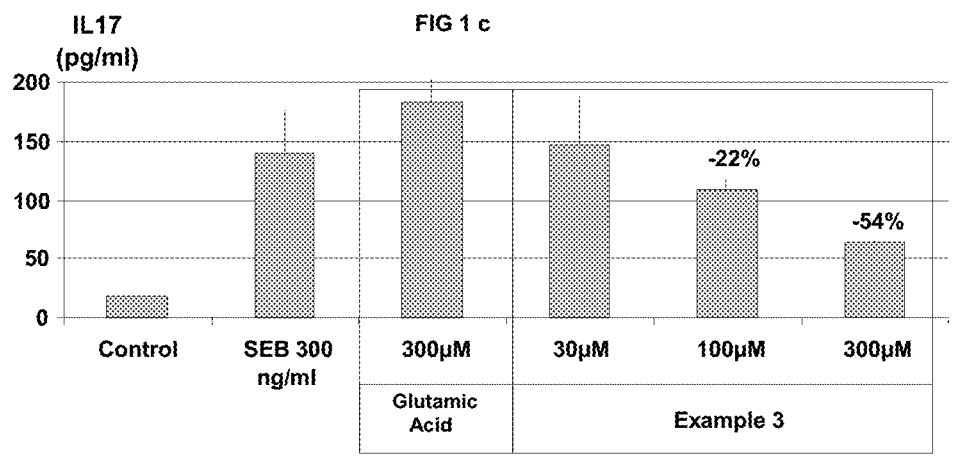

The modulation of the observed immune response is illustrated by the appended drawings wherein:

FIG. 1: Demonstration of the immuno-regulatory activity of the compound according to Example 3 vs. glutamic acid towards productions of IL-2 (1a), IL 4 (1b) and IL-17 (1c) by human lymphocytes; this activity is dose-dependent and attains 63%, 70% and 54% inhibition of the productions of IL-2, IL-4 and IL-17 respectively at the concentration of 300 µM.

Figure 2A:
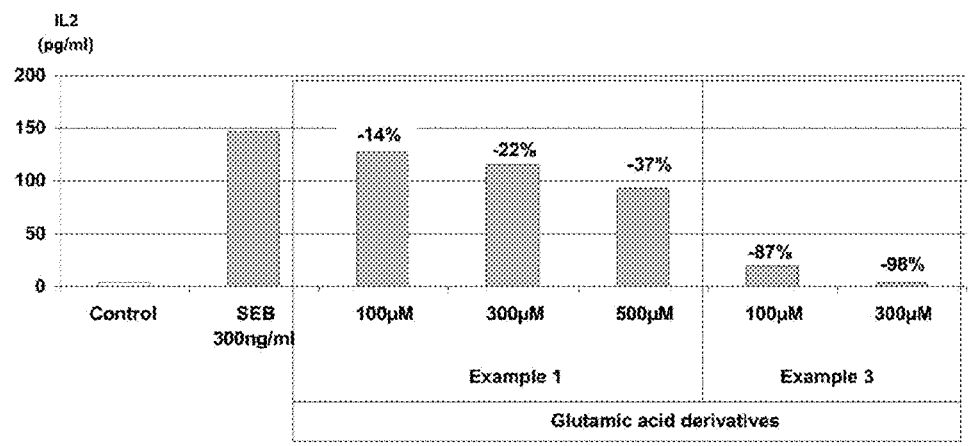
FIGS. 2a, 2b and 2c: Demonstration of the immunoregulatory activity of alkyl derivatives with a linear short chain (2a), with a linear long chain (2b) and with a branched short chain (2c) towards secretion of IL-2 by human lymphocytes.
Figure 2B:
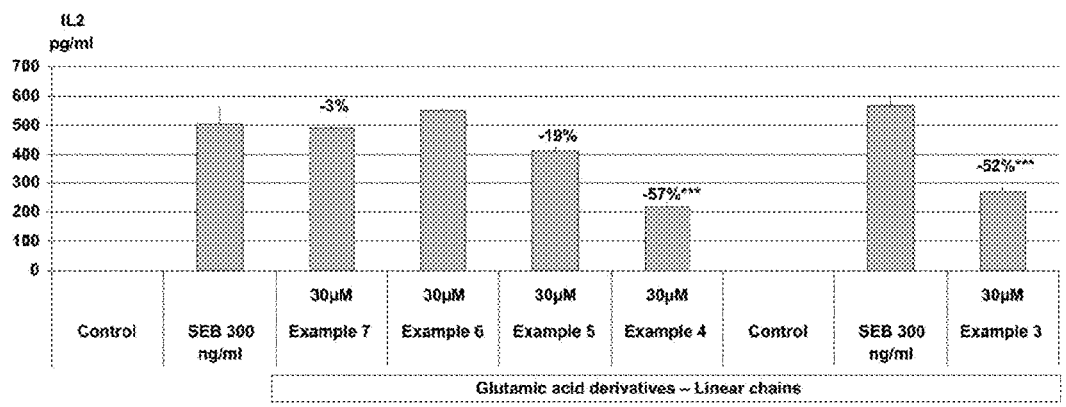
Figure 2C:
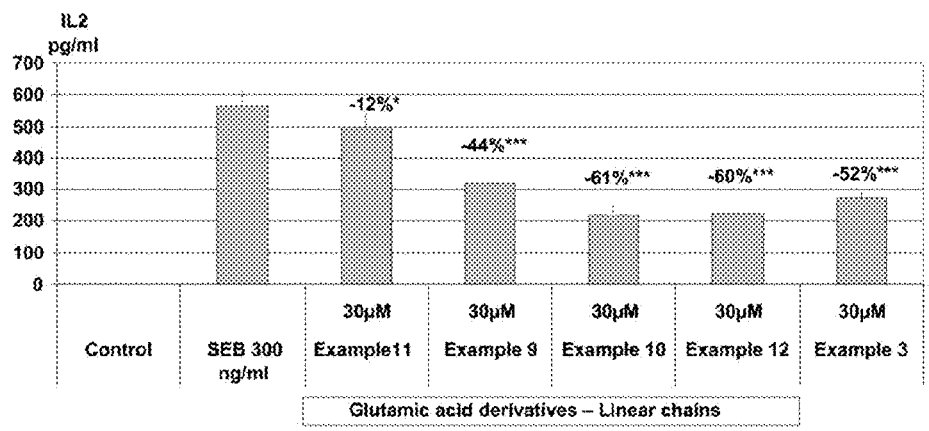

FIG. 2: Demonstration of the immuno-regulatory activity of alkyl derivatives with a linear short chain (2a), with a linear long chain (2b) and with a branched short chain (2c) towards the secretion of IL-2 by human lymphocytes; the activity is optimum for compounds for which the chain lengths are comprised between $C_5$ and $C_{14}$ in the presence of a short branched chain gives the possibility of maintaining this activity comparatively with the compound according to Example 3.

Figures 3, 4:
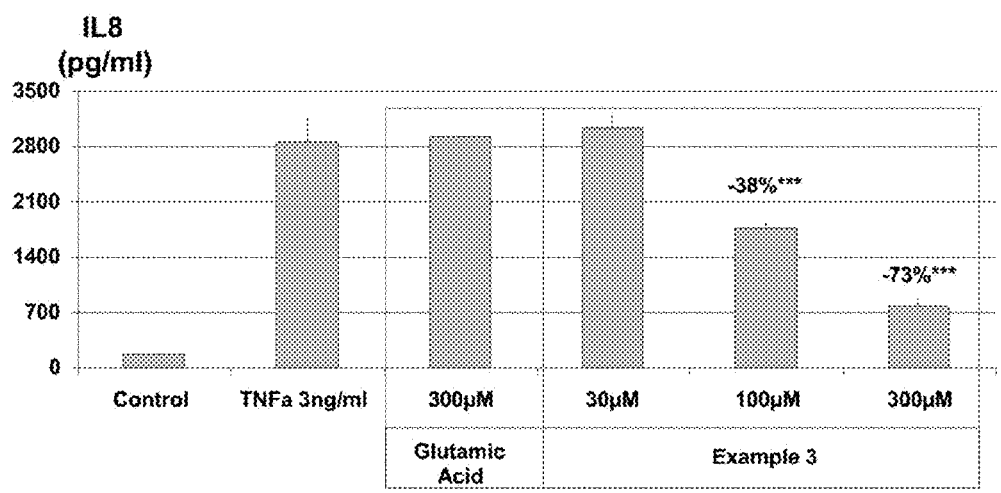
FIG. 3: Demonstration of the immuno-regulatory activity of the compound according to Example 12 towards secretions of cytokines involved in the immune responses of types Th 1, Th2 and Th17.
FIG. 4: Demonstration of the anti-inflammatory activity of the compound according to Example 3 towards the production of IL-8 by human keratinocytes.

FIG. 3: Demonstration of the immuno-regulatory activity of the compound according to Example 12 towards productions of the cytokines Th1, Th2, Th17 by human lymphocytes; this activity is dose-dependent and attains 43%, 44%, 77%, 80%, 18% inhibition of the productions of IL2, IL6, IFNγ, IL1β, TNFα, 69%, 77%, 87%, 84% inhibition of the productions of IL4, IL5, IL10, IL13, and 86% inhibition of the production of IL17 at the concentration of 300 µM.

The presence of lipophilicity on the glutamate unit allows modulation of the lymphocyte activation of the TH2, TH17 and TH1 induced by the (SEB) B enterotoxin, a superantigen of Staphylococcus aureus.

A.2—Demonstration of the anti-inflammatory activity: Study of the secretion of IL8 for the keratinocyte response.

The HaCaT keratinocytes distributed in 24-well plates are pre-incubated for 2 hours with the active ingredients to be evaluated and then stimulated for 24 hours with 10 ng/ml of TNFα. The dosage of interleukin 8 is carried out from a sample taken from the supernatant according to the following method:

IL8 is evaluated by ELISA, Duoset IL8 (Ref. DY208E, R&D Systems).

The modulation of the inflammatory response observed is illustrated by the appended drawing wherein:

FIG. 4: Demonstration of the antiinflammatory activity of Example 3 vs. glutamic acid towards the production of IL-8.

SYNTHESIS EXAMPLES FOR THE COMPOUNDS ACCORDING TO THE INVENTION

Procedure 1

This procedure is adapted from those described in patent FR 1 427 996, MERCK & CO, 1965.

Example 1

5(n-pentyl)-L-glutamate or 2-amino-5-oxo-5-(pentyloxy)pentanoic acid

L-glutamic acid (3 g, 1 equiv.) is suspended in a mixture of tert-butanol (10.5 equiv.) and pentanol (99%, 4 equiv.). After heating the reaction medium to 40° C., 95% $H_2SO_4$ (1.5 equiv.) is added dropwise. The heating temperature is then increased up to 65° C. until a limpid solution is obtained. Finally, the temperature is maintained for 20 hours at 65° C. After having stopped the heating, triethylamine (0.57 equiv.) is added dropwise to the reaction mixture as rapidly as possible. Then are added 5 ml of water and 66 ml of ethanol. Finally, at room temperature, 2.1 equiv. of triethylamine are added which initiates precipitation. The reaction medium is then left with stirring for 30 minutes. The precipitate is then filtered and then dried for one hour in vacuo at 50° C. and washed with 13 ml of ethanol and then with 13 ml of diethyl ether. The obtained product is dried in vacuo at 30° C. for one night and then recrystallized by adding 40 ml of an isopropanol:water (1:1) solution and by heating to 83° C. until complete dissolution. The mixture is then brought back to room temperature and the product crystallizes. The precipitate is then washed with 4 ml of an isopropanol:water (1:1) mixture and then with 13 ml of ethanol and finally 13 ml of diethyl ether. The obtained product is isolated in the form of white crystals.

Yield: 10%

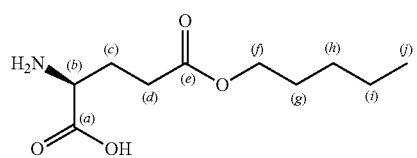

NMR ($^1$H, D$_2$O): δ (ppm): 0.9 (t, 3H, CH$_{3(j)}$); 1.3 (m, 4H, CH$_{2(i-h)}$); 1.7 (quint, 2H, CH$_{2(g)}$); 2.1 (m, 2H, CH$_{2(c)}$); 2.6 (m, 2H, CH$_{2(d)}$); 3.7 (t, 1H, CH$_{(b)}$); 4.1 (t, 2H, CH$_{2(f)}$).

NMR ($^{13}$C, D$_2$O): δ (ppm):16.1 (CH$_{3(j)}$); 24.5 (CH$_{2(i)}$); 28.4 (CH$_{2(c)}$); 30.2 (CH$_{2(h)}$); 30.3 (CH$_{2(g)}$); 32.9 (CH$_{2(d)}$); 56.9 (CH$_{(b)}$); 68.9 (CH$_{2(f)}$); 174.5 (C$_{(e)}$); 177.9 (C$_{(a)}$).

MS: ESI+: [M+H]$^+$: 218.2 (100%)

Example 2

5(-n-hexyl)-L-glutamate or 2-amino-5-(hexyloxy)-5-oxopentanoic acid

L-glutamic acid (3 g, 1 equiv.) is suspended in a mixture of tertbutanol (10.5 equiv.) and hexanol (99%, 4 equiv.). After heating the reaction medium to 40° C., 95% H$_2$SO$_4$ (1.5 equiv.) is added dropwise. The heating temperature is then increased up to 65° C. until a limpid solution is obtained. Finally, the temperature is maintained for one hour at 65° C. After having stopped the heating, triethylamine (0.57 equiv.) is added dropwise to the reaction mixture as rapidly as possible. Then are added 5 ml of water and 66 ml of ethanol. Finally, at room temperature, 2.1 equiv. of triethylamine are added, which initiates precipitation. The reaction medium is then left with stirring for 30 minutes. The precipitate is then filtered and then dried for one hour in vacuo at 50° C. and washed with 13 ml of ethanol and then with 13 ml of diethyl ether. The obtained product is dried in vacuo at 30° C. for one night and then recrystallized by adding 40 ml of an isopropanol:water (1:1) solution and by heating to 83° C. until complete dissolution. The mixture is then brought back to room temperature and the product crystallizes. The precipitate is then washed with 4 ml of the isopropanol:water (1:1) mixture and then with 13 ml of ethanol and finally with 13 ml of diethyl ether. The obtained product is isolated as white crystals.

Yield: 17%

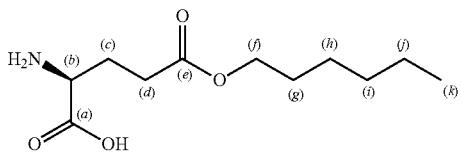 [SMILES: CCCCCCOC(=O)CC[C@H](N)C(=O)O]

NMR ($^1$H, D$_2$O): δ (ppm): 0.88 (t, 3H, CH$_{3(k)}$); 1.3 (m, 6H, CH$_{2(j-h)}$); 1.7 (quint, 2H, CH$_{2(g)}$); 2.1 (m, 2H, CH$_{2(c)}$); 2.6 (m, 2H, CH$_{2(d)}$); 3.7 (t, 1H, CH$_{(b)}$); 4.1 (t, 2H, CH$_{2(f)}$).

NMR ($^{13}$C, D$_2$O):δ (ppm):16.2 (CH$_{3(k)}$); 24.8 (CH$_{2(j)}$); 27.7 (CH$_{2(c)}$); 28.4 (CH$_{2(h)}$); 30.6 (CH$_{2(g)}$); 32.9 (CH$_{2(d)}$); 33.6 (CH$_{2(i)}$); 56.9 (CH$_{(b)}$); 68.9 (CH$_{2(f)}$); 174.5 (C$_{(e)}$); 177.9 (C$_{(a)}$).

MS: ESI+: [M+H]$^+$: 232.1 (100%)

Example 3

5-(n-nonyl)-L-glutamate or 2-amino-5-(nonyloxy)-5-oxopentanoic acid

L-glutamic acid (3 g, 1 equiv.) is suspended in a mixture of tert-butanol (10.5 equiv.) and nonanol (99%, 4 equiv.). After heating the reaction medium to 40° C., 95% H$_2$SO$_4$ (1.5 equiv.) is added dropwise. The heating temperature is then increased up to 65° C. until a limpid solution is obtained. Finally, the temperature is maintained for four hours at 65° C. After having stopped the heating, triethylamine (0.57 equiv.) is added dropwise to the reaction mixture as rapidly as possible. Then are added 5 ml of water and 66 ml of methanol. Finally, at room temperature, 2.1 equiv. of triethylamine are added, which initiates precipitation. The reaction medium is then left with stirring for 30 minutes. The precipitate is then filtered and resuspended in about 50 ml of distilled water. The mixture is subjected to stirring and heated to 65° C. for 20 min. The precipitate is again filtered, washed with 13 ml of methanol and then 13 ml of diethyl ether. The obtained product is dried in vacuo 25° C. for one night and then recrystallized by adding 50 ml of an isopropanol:water (1:1) solution and by refluxing the isopropanol with heating until complete dissolution. The mixture is then brought back to room temperature and the product crystallizes. The precipitate is then washed with 5 ml of the isopropanol:water (1:1) mixture and then with 15 ml of methanol and finally 15 ml of diethyl ether. The product is isolated as white crystals and dried in vacuo at 20° C. for one night.

Yield: 40%

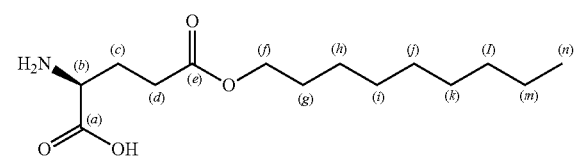

NMR ($^1$H, MeOD): δ (ppm): 0.9 (t, 3H, CH$_{3(n)}$); 1.3 (m, 12H, CH$_{2(m-h)}$); 1.7 (quint, 2H, CH$_{2(g)}$); 2.1 (m, 2H, CH$_{2(c)}$); 2.5 (t, 2H, CH$_{2(d)}$); 3.6 (t, 1H, CH$_{(b)}$); 4.1 (t, 2H, CH$_{2(f)}$).

NMR ($^{13}$C, MeOD): δ (ppm): 14.5 (CH$_{3(n)}$); 23.7 (CH$_{2(m)}$); 27.1 (CH$_{2(c)}$); 27.5 (CH$_{2(h)}$); 29.8 (CH$_{2(g)}$); 30.4 (CH$_{2(k)}$); 30.5 (CH$_{2(i)}$); 31.1 (CH$_{2(j)}$); 33.1 (CH$_{2(d)}$); 33.1 (CH$_{2(l)}$); 55.5 (CH$_{(b)}$); 66.0 (CH$_{2(f)}$); 174.5 (C$_{(e)}$); 177.9 (C$_{(a)}$).

Anal. Calculated for C$_{14}$H$_{27}$N$_2$O$_4$ (273.37): theoretically: C 61.51; H 9.96; N 5.12; Experiment: C 61.80; H 9.96; N 4.72

MS: ESI+: [M+H]$^+$: 274.2 (100%)

Example 4

5-(n-dodecyl)-L-glutamate or 2-amino-5-(dodecyloxy)-5-oxopentanoic acid

L-glutamic acid (5 g, 1 equiv.) is suspended in a mixture of tert-butanol (34 ml, 10.5 equiv.) and of 1-dodecanol (22.9 g, 3.6 equiv.). The reaction medium is heated to 40° C. 95% H$_2$SO$_4$ (2.9 ml) is added dropwise. The suspension is heated to 65° C. After one hour and a half, a homogenous solution is obtained. The mixture is stirred for a further one hour at 65° C. and the heating is cut off. After returning to room temperature, triethylamine (2.7 ml) is added dropwise within 1 minute. Next, water (8 ml) and ethanol (119 ml) are added, followed by triethylamine (10.2 ml). After 30 minutes of stirring, the white precipitate is filtered and dried. The thereby obtained pasty white solid is triturated in water (91 ml) at 65° C. The solid is filtered, washed with methanol (23 ml) and then with diethyl ether (23 ml) and dried in vacuo. The obtained white powder (5.72 g) is then triturated in an isopropanol:water (2:1) (160 ml) mixture at 85° C. The mixture is cooled to room temperature and the expected product is filtered on a frit, rinsed with an isopropanol:water (2:1) (50 ml) mixture and then with methanol (50 ml) and with diethyl ether (50 ml). The product is dried in vacuo for one night and then triturated in water (100 ml) and finally crystallized a second time in an isopropanol:water (2:1) (150 ml) mixture.

The product is finally isolated in the form of white crystals and dried in vacuo at 20° C. for one night.

Yield 43%

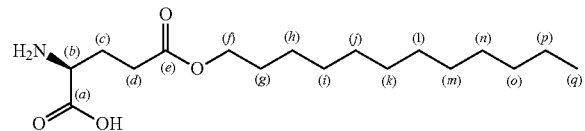

MP: 189.9° C.

NMR ($^1$H, CF$_3$COOD, 300 MHz): δ (ppm): 0.9 (t, 3H, CH$_{3(q)}$); 1.3 (m, 18H, CH$_{2(p-h)}$); 1.8 (m, 2H, CH$_{2(g)}$); 2.5 (m, 2H, CH$_{2(c)}$); 2.95 (t, 2H, CH$_{2(d)}$); 4.3 (t, 2H, CH$_{2(f)}$); 4.58 (m, 1H, CH$_{(b)}$).

NMR ($^{13}$C, CF$_3$COOD, 75 MHz): δ (ppm): 12.3 (CH$_{3(q)}$); 21.9 (CH$_{2(p)}$); 24.2 (CH$_{2(c)}$); 25.01 (CH$_{2(h)}$); 27.5 (CH$_{2(g)}$); 28.5-29.01 (CH$_{2(i-n)}$); 30.01 (CH$_{2(d)}$); 31.3 (CH$_{2(o)}$); 53.4 (CH$_{(b)}$); 67.6 (CH$_{2(f)}$); 172.5 (C$_{(e)}$); 176.6 (C$_{(a)}$).

Anal. Calculated for C$_{17}$H$_{33}$NO$_4$ (315.24): theoretically: C 64.73; H 10.54; N 4.44; Experiment: C 64.57; H 10.69; N 4.10

MS: ESI+: [M+H]$^+$: 316.2; ESI−: [M−H]$^−$: 314.2

Example 5

5-(n-tetradecyl)-L-glutamate or 2-amino-5-oxo-5(tetradecyl)pentanoic acid

This compound isolated as a white solid was obtained with a yield of 51% according to the procedure used for preparing L-glutamic acid 5 dodecyl ester with 4 g of glutamic acid and 23.3 g of tetradecanol.

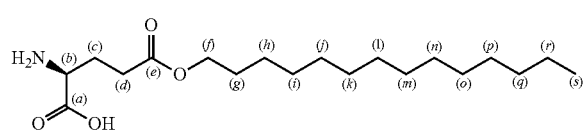

MP: 184.8° C.

NMR ($^1$H, CF$_3$COOD, 300 MHz): δ (ppm): 0.9 (t, 3H, CH$_{3(s)}$); 1.3-1.4 (m, 22H, CH$_{2(r-h)}$); 1.8 (m, 2H, CH$_{2(g)}$); 2.5 (m, 2H, CH$_{2(c)}$); 2.95 (t, 2H, CH$_{2(d)}$); 4.3 (t, 2H, CH$_{2(f)}$); 4.58 (m, 1H, CH$_{(b)}$).

NMR ($^{13}$C, CF$_3$COOD, 75 MHz): δ (ppm): 12.2 (CH$_{3(s)}$); 21.9 (CH$_{2(r)}$); 24.2 (CH$_{2(c)}$); 25.01 (CH$_{2(h)}$); 27.5 (CH$_{2(g)}$); 28.5-29.07 (CH$_{2(i-p)}$); 30.00 (CH$_{2(d)}$); 31.4 (CH$_{2(q)}$); 53.4 (CH$_{(b)}$); 67.6 (CH$_{2(f)}$); 172.5 (C$_{(e)}$); 176.6 (C$_{(a)}$).

Anal. Calculated for C$_{19}$H$_{37}$NO$_4$ (343.27): theoretically: C 66.43; H 10.86; N 4.08; Experiment: C 65.66; H 10.58; N 3.94

MS: ESI+: [M+H]$^+$: 344.2; ESI−: [M−H]$^−$: 342.2

Example 6

5-(n-hexadecyl)-L-glutamate or 2-amino-5-(hexadecyloxy)-5-oxopentanoic acid

This compound isolated as a white solid was obtained with a yield of 69% according to the procedure used for preparing 5-(n-dodecyl)-L-glutamate with 5 g of glutamic acid and 33 g of hexadecanol.

MP: 179.3° C.

NMR ($^1$H, CF$_3$COOD, 300 MHz): δ (ppm): 0.8 (t, 3H, CH$_{3(u)}$); 1.23 (m, 26H, CH$_{2(t-h)}$); 1.65 (m, 2H, CH$_{2(g)}$); 2.4 (m, 2H, CH$_{2(c)}$); 2.8 (t, 2H, CH$_{2(d)}$); 4.16 (t, 2H, CH$_{2(f)}$); 4.43 (m, 1H, CH$_{(b)}$).

NMR ($^{13}$C, CF$_3$COOD, 75 MHz): δ (ppm): 12.2 (CH$_{3(u)}$); 21.9 (CH$_{2(t)}$); 24.1 (CH$_{2(c)}$); 24.9 (CH$_{2(h)}$); 27.4 (CH$_{2(g)}$); 28.4-28.9 (CH$_{2(i-r)}$); 29.8 (CH$_{2(d)}$); 31.3 (CH$_{2(s)}$); 53.2 (CH$_{(b)}$); 67.4 (CH$_{2(f)}$); 172.3 (C$_{(e)}$); 176.5 (C$_{(a)}$).

Anal. Calculated for C$_{21}$H$_{41}$NO$_4$ (371.55): theoretically: C 67.88; H 11.12; N 3.77; Experiment: C 67.60; H 10.93; N 3.77

MS: ESI+: [M+H]$^+$: 372.3; ESI−: [M−H]$^−$: 370.2

Example 7

5-(n-octadecyl)-L-glutamate or 2-amino-5-(octadecyloxy)-5-oxopentanoic acid

This compound is isolated as a white solid with a yield of 45% according to the procedure used for preparing 5-(n-dodecyl)-L-glutamate ester with 2.5 g of glutamic acid and 18.1 g of octadecanol.

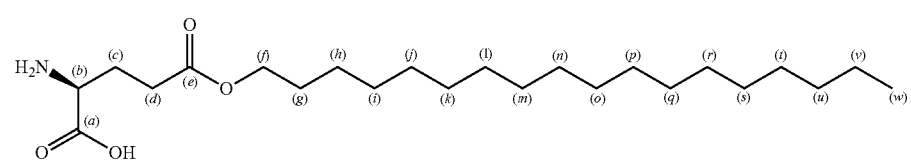

MP: 180.5° C.

NMR ($^1$H, CF$_3$COOD, 300 MHz): δ (ppm): 0.8 (t, 3H, CH$_{3(w)}$); 1.3 (m, 30H, CH$_{2(v-h)}$); 1.7 (m, 2H, CH$_{2(g)}$); 2.5 (m, 2H, CH$_{2(c)}$); 2.9 (t, 2H, CH$_{2(d)}$); 4.2 (t, 2H, CH$_{2(f)}$); 4.5 (m, 1H, CH$_{(b)}$).

NMR ($^{13}$C, CF$_3$COOD, 75 MHz): δ (ppm): 12.2 (CH$_{3(w)}$); 21.9 (CH$_{2(v)}$); 24.1 (CH$_{2(c)}$); 24.9 (CH$_{2(h)}$); 27.5 (CH$_{2(g)}$); 28.5-29.01 (CH$_{2(i-t)}$); 29.9 (CH$_{2(d)}$); 31.3 (CH$_{2(u)}$); 53.3 (CH$_{(b)}$); 67.5 (CH$_{2(f)}$; 172.4 (C$_{(e)}$); 176.6 (C$_{(a)}$).

Anal. Calculated for C$_{23}$H$_{45}$N0$_4$ (399.61): theoretically: C 69.13; H 11.35; N 3.51; Experiment: C 68.69; H 11.36; N 3.38

MS: ESI+: [M+H]$^+$: 400.3; ESI−: [M−H]$^-$: 398.3

Example 8

5-(3,7-dimethyloctyl)-L-glutamate or 2-amino-5(3,7-dimethyloctyloxy)-5-oxo-pentanoic acid This compound is isolated as a white solid with a yield of 51% according to the procedure used for preparing 5-(n-dodecyl)-L-glutamate ester with 3 g of glutamic acid and 15.6 ml of 3,7-dimethyl-1-octanol.

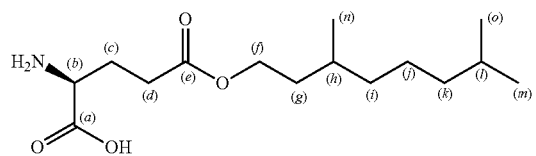

MP: 150.8° C.

NMR ($^1$H, CF$_3$COOD, 300 MHz): δ (ppm): 0.95 (m, 6H, CH$_{3(m+o)}$); 0.98 (m, 3H, CH$_{3(n)}$); 1.3-1.4 (m, 6H, CH$_{2(i-k)}$); 1.7 (m, 3H, CH$_{2(g)}$+CH$_{(l)}$); 1.9 (m, 1H, CH$_{(h)}$); 2.5 (m, 2H, CH$_{2(c)}$); 2.9 (m, 2H, CH$_{2(d)}$); 4.4 (t, 2H, CH$_{2(f)}$); 4.6 (m, 1H, CH$_{(b)}$).

NMR ($^{13}$C, CF$_3$COOD, 75 MHz): δ (ppm): 17.3 (CH$_{3(n)}$); 20.5 (CH$_{3(m)}$+CH$_{3(o)}$); 23.7 (CH$_{2(c)}$+CH$_{2(j)}$); 27.06 (CH$_{(l)}$); 29.07 (CH$_{(h)}$); 29.7 (CH$_{2(d)}$); 34.15 (CH$_{2(g)}$); 36.16 (CH$_{2(i)}$); 38.3 (CH$_{2(k)}$); 53.05 CH$_{(b)}$); 65.8 (CH$_{2(f)}$); 172.2 (C$_{(e)}$); 176.3 (C$_{(a)}$).

Anal. Calculated for C$_{15}$H$_{29}$NO$_4$ (287.4): theoretically: C 62.69; H 10.17; N 4.87; Experiment: C 62.42; H 10.26; N 4.64

MS: ESI+: [M+H]$^+$: 288.3; ESI−: [M−H]$^-$: 286.3

Procedure 2

Synthesis using (S)-5-(benzyloxy)-4-(benzyloxycarbonylamino)-5-oxopentanoic acid as a starting product. The functions protected by benzyls are then de-protected by catalytic hydrogenation.

Demonstration of the immuno-regulatory activity on IL2

The test described earlier shows that this compound of Example 8 is provided with a significant activity of 29% at 300 μM on the secretion of IL2.

Example 9

5-(n-nonan-2-yl)-L-glutamate or 2-amino-5(nonan-2-yloxy)-5-oxopentanoic acid

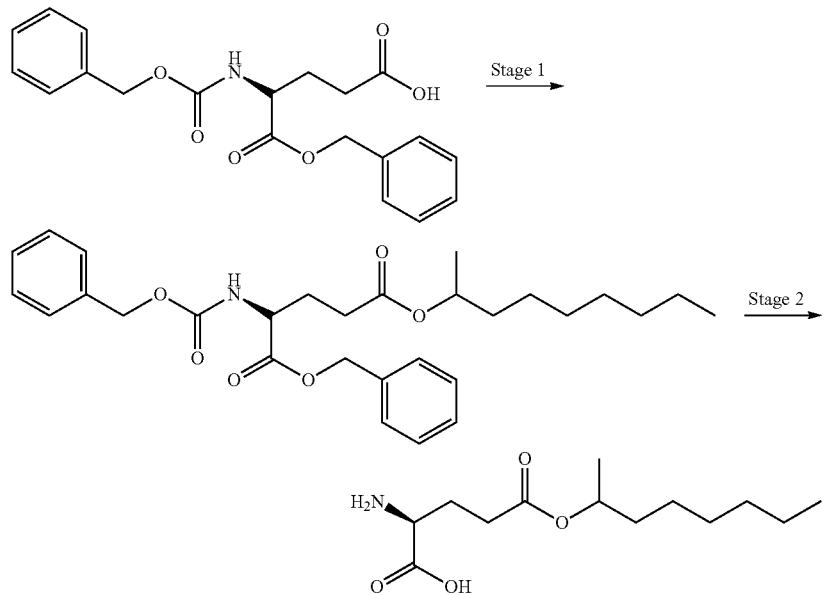

Equipment: 250 ml one-neck flask provided with magnetic stirring and placed under sweeping with nitrogen.

The alpha-(n-benzyl)-L-glutamate-N-alpha-benzylcarbonyl acid (5 g, 1 equiv.), 2-nonanol (2.92 g, 1,5 equiv.), EDCI (2.58 g, 1 equiv.), HOBT (1.82 g, 1 equiv.) and DMAP (1.65 g, 1 equiv.) are suspended in dichloromethane (100 ml). The reaction medium is stirred at room temperature overnight. The medium is successively washed with a 0.1N hydrochloric acid solution, a saturated sodium hydrogencarbonate solution and then with a saturated sodium chloride solution. The organic phase is dried on magnesium sulphate, filtered and concentrated in order to lead to a pale yellow oil which is then purified by chromatography on silica gel (heptane: ethyl acetate gradient (100:0 to 50:50) in order to lead to a yellow oil (2.65 g, yield 40%) which will be reengaged into stage 2.

The assembly is set under an inert atmosphere (nitrogen). The yellow oil is put into solution in methanol (132 ml) and palladium on coal (10%, 566 mg) is added. The medium is hydrogenated at room temperature overnight and then filtered on celite. The filtrate is dry concentrated in order to lead to a white solid which will be triturated in methanol (10 ml) at 0° C. for one hour. The solid is then filtered on a frit, rinsed with icy methanol and dried in order to lead to a white solid (1 g, yield 69%).

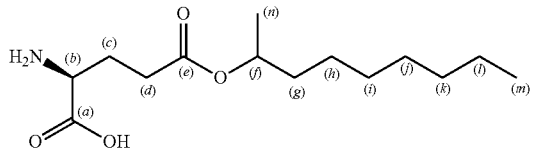

NMR ($^1$H, CF$_3$COOD, 300 MHz): δ (ppm): 0.9 (t, 3H, CH$_{3(m)}$); 1.3 (m, 13H, CH$_{3(n)}$+CH$_{2(h-l)}$), 1.7 (m, 2H, CH$_{2(g)}$); 2.5 (m, 2H, CH$_{2(d)}$); 2.9 (t, 2H, CH$_{2(d)}$); 4.5 (m, 1H, CH$_{(f)}$); 5.1 (m, 1H, CH$_{(b)}$).

NMR ($^{13}$C, CF$_3$COOD, 75 MHz): δ (ppm): 12.3 (CH$_{3(m)}$); 17.6 (CH$_{2(n)}$); 21.7 (CH$_{2(l)}$); 24.2 (CH$_{2(c)}$); 24.6 (CH$_{2(h)}$); 28.4-28.5 (CH$_{2(i-j)}$); 30.2 (CH$_{2(d)}$); 30.3 (CH$_{2(k)}$); 34.9 (CH$_{2(g)}$); 53.3 (CH$_{(b)}$); 75.8 (CH$_{2(f)}$); 172.5 (C$_{(e)}$); 176.1 (C$_{(a)}$).

Anal. Calculated for C$_{14}$H$_{27}$NO$_4$ (273.37): theoretically: C 61.51; H 9.96; N 5.12; Experiment: C 61.63; H 9.67; N 5.07

MS: ESI+: [M+H]$^+$: 274.3; ESI−: [M−H]$^−$: 272.2

Example 10

5-(n-nonan-5-yl)-L-glutamate or 2-amino-5(nonan-5-yloxy)-5-oxopentanoic acid

This compound is obtained under the same operating conditions as those used for isolating the compound 5-(n-nonan-2-yl)-L-glutamate. Only trituration in methanol in the last stage was not applied because of the partial solubility of this product in this solvent.

Stage 1: 1.98 g of yellow oil which crystallizes over time, yield 60%.

Stage 2: 300 mg, yield 68%

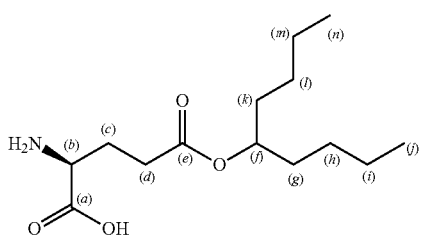 [SMILES: CCCCC(CCCC)OC(=O)CC[C@H](N)C(=O)O]

NMR ($^1$H, CF$_3$COOD, 300 MHz): δ (ppm): 0.9 (m, 6H, CH$_{3(n)}$+CH$_{3(j)}$); 1.3 (m, 8H, CH$_{2(m+l+h+i)}$); 1.4 (m, 4H, CH$_{2(k+g)}$); 2.1 (m, 2H, CH$_{2(c)}$); 2.5 (m, 2H, CH$_{2(d)}$); 3.5 (m, 1H, CH$_{(f)}$); 4.8 (m, 1H, CH$_{(b)}$).

NMR ($^{13}$C, CF$_3$COOD, 75 MHz): δ (ppm): 17.5 (CH$_{3(j)}$+CH$_{3(n)}$); 24.04 (CH$_{2(l+m+h+i)}$); 28.8 (CH$_{2(c)}$); 31.5 (CH$_{2(d)}$); 35.3 (CH$_{2(g+k)}$); 55.7 (CH$_{(b)}$); 76.4 (CH$_{2(f)}$); 173.4 (C$_{(e)}$); 174.6 (C$_{(a)}$).

Anal. Calculated for C$_{14}$H$_{27}$NO$_4$ (273.37): theoretically: C 61.51; H 9.96; N 5.12; Experiment: C 61.17; H 9.91; N 5.03

MS: ESI+: [M+H]$^+$: 274.3; ESI−: [M−H]$^−$: 272.2

Example 11

5-(2-hexyldecyl)-L-glutamate or 2-amino-5(2-hexyldecyl oxy)-5-oxopentanoic acid

This compound is obtained under the same operating conditions as those used for isolating the compound 5-(nonan-2-yl)-L-glutamate. The low yield of the last stage is explained by partial solubility of the product in methanol.

Stage 1: 3.93 g of white solid, yield 57%
Stage 2: 440 mg of white solid, yield 18%

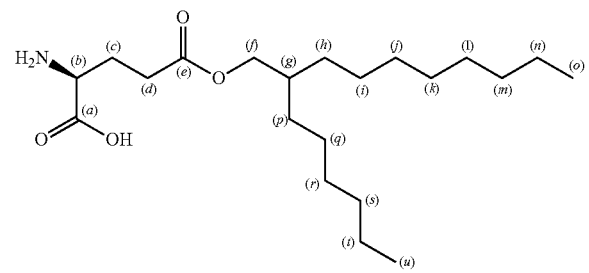

NMR ($^1$H, CF$_3$COOD, 300 MHz): δ (ppm): 0.9 (m, 6H, CH$_{3(o)}$+CH$_{3(u)}$); 1.3 (m, 24H, CH$_{2(h+i+j+k+l+m+n+p+q+r+s+t)}$); 1.7 (m, 1H, CH$_g$); 2.5 (m, 2H, CH$_{2(c)}$); 2.9 (m, 2H, CH$_{2(d)}$); 4.2 (m, 2H, CH$_{2(f)}$); 4.5 (m, 1H, CH$_{(b)}$).

NMR ($^{13}$C, CF$_3$COOD, 75 MHz): δ (ppm): 12.1 (CH$_{3(O)}$+CH$_{3(u)}$); 21.7 (CH$_{2(n+t)}$); 24.1 (CH$_{2(c)}$); 25.8 (CH$_{2(i+q)}$); 28.6-31.2 (CH$_{2(d+j+k+r+h+p+m+l+s)}$); 36.7 (CH$_g$); 53.3 (CH$_{(b)}$); 70.3 (CH$_{2(f)}$); 172.4 (C$_{(e)}$); 176.6 (C$_{(a)}$).

Anal. Calculated for C$_{21}$H$_{41}$NO$_4$ (371.3): theoretically: C 67.88; H 11.12; N 3.77; Experiment: C 67.78; H 11.08; N 3.76

MS: ESI+: [M+H]$^+$: 372.3; ESI−: [M−H]$^−$: 370.3

Example 12

5-(2-ethylhexyl)-L-glutamate or 2-amino-5(2-ethylhexyl oxy)-5-oxopentanoic acid

This compound is obtained under the same operating conditions as those used for isolating the compound 5-(nonan-2-yl)-L-glutamate. An alternative occurs at the treatment of stage 2. Indeed, after filtration on celite, the filtrate is concentrated down to about 50 ml. Diisopropyl ether (200 ml) is added and the formed mixture is placed at −18° C. overnight. The thereby obtained suspension is filtered and the white solid is dried in vacuo.

Stage 1: 4.22 g of colourless oil, yield 65%
Stage 2: 1.5 g of a white solid, yield 70%

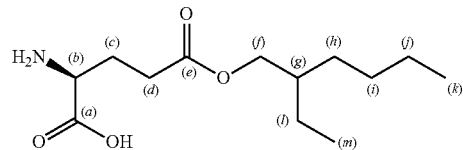 [SMILES: CCCCC(CC)COC(=O)CC[C@H](N)C(=O)O]

MP: 157.9° C.

NMR ($^1$H, CF$_3$COOD, 300 MHz): δ (ppm): 0.9 (m, 6H, CH$_{3(k)}$+CH$_{3(m)}$); 1.4 (m, 8H, CH$_{2(h+i+j+l)}$); 1.7 (m, 1H, CH$_g$); 2.6 (m, 2H, CH$_{2(c)}$); 2.9 (m, 2H, CH$_{2(d)}$); 4.2 (m, 2H, CH$_{2(f)}$); 4.5 (m, 1H, CH$_{(b)}$).

NMR ($^{13}$C, CF$_3$COOD, 75 MHz): δ (ppm): 8.9 (CH$_{3(m)}$); 11.9 (CH$_{3(k)}$); 22.0 (CH$_{2(j)}$); 22.8 (CH$_{2(l)}$); 24.2 (CH$_{2(c)}$); 28.2 (CH$_{2(i)}$); 29.5 (CH$_{2(h)}$); 29.9 (CH$_{2(d)}$); 38.3 (CH$_g$); 53.3 (CH$_{(b)}$); 69.9 (CH$_{2(f)}$); 172.5 (C$_{(e)}$); 176.6 (C$_{(a)}$).

Anal. Calculated for C$_{13}$H$_{25}$NO$_4$ (259.2): theoretically: C 60.21; H 9.72; N 5.40; Experiment: C 60.08; H 9.59; N 5.45

MS: ESI+: [M+H]$^+$: 260.2; ESI−: [M−H]$^-$: 258.1

Evaluation on a Keratinocyte Model of the Compound According to Example 12:

Demonstrating the anti-inflammatory activity on keratinocytes expressing a phenotype of atopic dermatitis (AD): Study of the overexpressed cytokines and chemokines in the pathology of atopic dermatitis.

The primary keratinocytes (NHEK, normal human epidermal keratinocytes) distributed in 24-well plates are pre-incubated for 1 hour with the active ingredients and then stimulated for 24 hours with a cocktail of 4 agonists giving the possibility of creating in vitro the physio-pathological environment of atopic dermatitis: 100 ng/ml IL4+100 ng/ml IL13+1 µg/ml Poly I:C+5 µg/ml Pam3CSK4: this model gives the possibility of inducing the inflammation mediated by the overexpressed Th2 cytokines in DA (IL4, IL13) and by the bacterial components (mimicked by Pam3CSK4, TLR-2 ligand) and viral components (mimicked by Poly I:C, TLR-3 ligand) of DA. Analysis of the gene expression of the markers of DA is conducted in a PCR-Array with 48 genes and repeated on 3 different donors of NHEK.

The modulation of the inflammatory response observed is illustrated by the appended table wherein:

For the whole of the markers, the RQ (Relative Quantity) of less than 0.5, at 5 h or 24 h, indicates significant inhibition:

- inhibition of the TSLP marker involved in the lymphocyte Th2 polarization and specific of AD;
- inhibition of the inflammatory cytokines IL1A, IL8, CSF2, IFNB1, VEGF;
- inhibition of the chemokines CCL, CXCL, involved in the recruitment, cutaneous infiltration, and activation of the inflammatory cells (leucocytes, lymphocytes, Th1 and Th2 lymphocytes, monocytes).

The obtained results of the demonstration of the anti-inflammatory activity of Example 12 towards the gene expression of the inflammatory markers of DA, the cytokines and chemokines are given in the table hereafter:

| NHEK keratinocytes: markers of the inflammation induced by 100 ng/ml IL4 + 100 ng/ml IL13 + 1 µg/ml Poly I:C + 5 µg/ml Pam3CSK4 | | Activity at 24 h of the compound according to Ex. 12 | |
|---|---|---|---|
| | | 100 µM | 300 µM |
| Cytokines | | | |
| Interleukin 1, alpha | IL1A | 0.53 | 0.53 |
| Interleukin 8 | IL8 | 0.29 | 0.18 |
| Thymic stromal lymphopoietin | TSLP | 0.20 | 0.54 |
| GMCSF, granulocyte-macrophage colony stimulating factor 2 | CSF2 | 1.55 | 0.33 |
| Interferon beta 1 | IFNB1 | 0.19 | 0.26 |
| Vascular endothelial growth factor C | VEGFC | 0.20 | 0.50 |

| NHEK keratinocytes: markers of the inflammation induced by 100 ng/ml IL4 + 100 ng/ml IL13 + 1 µg/ml Poly I:C + 5 µg/ml Pam3CSK4 | | Activity at 24 h of the compound according to Ex. 12 | |
|---|---|---|---|
| | | 100 µM | 300 µM |
| Chemokines | | | |
| MCP-1, Monocyte chemoattractant protein 1 | CCL2 | 0.48 | nd |
| MIP-1α, Macrophage inflammatory protein 1-alpha | CCL3 | 0.51 | 0.06 |
| MIP-1β, Macrophage inflammatory protein 1-beta | CCL4 | 0.14 | 0.02 |
| RANTES, Regulated on Activation, Normal T cell Expressed and Secreted | CCL5 | 0.42 | 0.20 |
| MIP-3α, Macrophage inflammatory protein 3-alpha | CCL20 | 0.13 | 0.13 |
| GRO-α, Melanoma growth stimulating activity, alpha | CXCL1 | 0.33 | 0.36 |
| MIP-2α, Macrophage inflammatory protein 2-alpha | CXCL2 | 0.06 | 0.32 |
| CXCL9, Gamma-interferon-induced monokine | CXCL9 | 0.20 | 0.29 |
| IP-10, 10 kDa Interferon gamma-induced protein | CXCL10 | 0.18 | 0.06 |
| I-TAC, Interferon-inducible T-cell alpha chemoattractant | CXCL11 | 0.14 | 0.15 |

Activities expressed in RQ (relative quantity) with respect to the stimulated control 100 ng/ml IL4 + 100 ng/ml IL13 + 1 µg/ml Poly I:C + 5 µg/ml Pam3CSK4/RQ < 0.5 = inhibition of the marker of the inflammation Example of a Formulation of an Active Ingredient According to the Present Invention The formulation was specifically developed for this type of compounds of formula I, in particular wherein the radical R is a linear or branched alkyl with 5 to 25 carbon atoms, generally having very low water-solubility.

The following formulation corresponds to the compound of Example 12, but may perfectly be generalized to other compounds of formula I with a C$_5$-C$_{25}$ alkyl substitution:

| | |
|---|---|
| Compound in Ex. 12 | 1.0 |
| Cyclomethicone | 3.5 |
| MYRITOL 318 emollient | 3.5 |
| CETIOL HE emollient | 3.5 |
| SEPIPLUS400 gelling agent | 3.0 |
| Propylene glycol | 9.0 |
| Phenoxyethanol | 0.2 |
| Purified water | qsp 100 ml |

The above formulation was prepared as follows:

Phase A: Heat the water and phenoxyethanol mixture to 75° C. Maintain heating and add the gelling agent with strong stirring.

Phase B: Mix the emollients and the silicone and heat this mixture to 75° C.

Phase C: Mix the propylene glycol and the compound according to Example 12: heat this mixture to 80° C. for 30 minutes.

Emulsify B in A and then add phase C.

The invention claimed is:

1. A method of topically treating and reducing the reoccurrence of inflammatory dermatoses comprising topically administering to a patient in need thereof, one or more compounds derived from L-glutamate of the following general formula I:

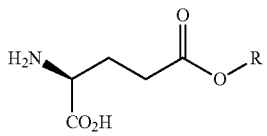 (I)

wherein the radical R represents
a linear or branched $C_5$-$C_{25}$ alkyl group,
or the benzyl radical,
or the phenethyl radical,
or a radical selected from the group consisting of isoprenyl, geranyl, farnesyl and phytyl radicals.

2. The method according to claim 1, wherein the radical R is a linear or branched $C_5$-$C_{25}$ alkyl group.

3. The method according to claim 1, wherein the radical R is a linear or branched $C_5$-$C_{14}$ alkyl group.

4. The method according to claim 1, wherein said one or more compounds is selected from:
   5-(n-pentyl)-L-glutamate or 2-amino-5-oxo-5-(pentyloxy)pentanoic acid
   5-(n-hexyl)-L-glutamate or 2-amino-5-(hexyloxy)-5-oxopentanoic acid
   5-(n-nonyl)-L-glutamate or 2-amino-5-(nonyloxy)-5-oxopentanoic acid
   5-(n-dodecyl)-L-glutamate or 2-amino-5-(dodecyloxy)-5-oxopentanoic acid
   5-(n-tetradecyl)-L-glutamate or 2-amino-5-oxo-5(tetradecyl)pentanoic acid
   5-(n-hexadecyl)-L-glutamate or 2-amino-5-(hexadecyloxy)-5-oxopentanoic acid
   5-(n-octadecyl)-L-glutamate or 2-amino-5-(octadecyloxy)-5-oxopentanoic acid
   5-(3,7-dimethyloctyl)-L-glutamate or 2-amino-5(3,7-dimethyloctyloxy)-5-oxo-pentanoic acid
   5-(nonan-2-yl)-L-glutamate or 2-amino-5(nonan-2-yloxy)-5-oxopentanoic acid
   5-(nonan-5-yl)-L-glutamate or 2-amino-5(nonan-5-yloxy)-5-oxopentanoic acid
   5-(2-hexyldecyl)-L-glutamate or 2-amino-5(2-hexyldecyloxy)-5-oxopentanoic acid
   5-(2-ethylhexyl)-L-glutamate or 2-amino-5(2-ethylhexyloxy)-5-oxopentanoic acid.

5. The method according to claim 1, wherein the inflammatory dermatosis is an atopic dermatitis, contact eczema, acne, seborrheic dermatitis, rosacea or psoriasis.

6. The method of claim 1, wherein the one or more compounds of formula I is administered as a topical composition comprising as an active ingredient the compound of formula I and at least one pharmaceutically or cosmetically acceptable excipient.

7. A compound derived from L-glutamic acid selected from the following compounds:
   5-(3,7-dimethyloctyl)-L-glutamate or 2-amino-5(3,7-dimethyloctyloxy)-5-oxopentanoic acid
   5-(nonan-5-yl)-L-glutamate or 2-amino-5(nonan-5-yloxy)-5-oxopentanoic acid
   5-(2-hexyldecyl)-L-glutamate or 2-amino-5(2-hexyldecyloxy)-5-oxopentanoic acid.

8. A method for preparing compounds of claim 7, which comprises
   reacting alpha-(n-benzyl)-L-glutamate-N-alpha-benzylcarbonyl acid with an alcohol of formula R—OH, wherein R represents
   a linear or branched $C_5$-$C_{25}$ alkyl group,
   or the benzyl radical,
   or the phenethyl radical,
   or a radical selected from the group consisting of isoprenyl, geranyl, farnesyl and phytyl radicals; and
   de-protecting the obtained product by catalytic hydrogenation.

\* \* \* \* \*